(12) United States Patent
Hungenberg et al.

(10) Patent No.: US 8,778,835 B2
(45) Date of Patent: Jul. 15, 2014

(54) PESTICIDAL COMPOSITION COMPRISING A PYRIDYLETHYLBENZAMIDE DERIVATIVE AND AN INSECTICIDE COMPOUND

(75) Inventors: Heike Hungenberg, Langenfeld (DE); Gilbert Labourdette, Paray le Monial (FR); Albert Schirring, Ratingen (DE); Burkhard Schuetz, Dusseldorf (DE); Anne Suty-Heinze, Langenfeld (DE); Wolfgang Thielert, Odenthal (DE); Martin Vaupel, Leichlingen (DE)

(73) Assignee: Bayer Cropscience AG, Monheim am Rhein (DE)

( * ) Notice: Subject to any disclaimer, the term of this patent is extended or adjusted under 35 U.S.C. 154(b) by 1013 days.

(21) Appl. No.: 12/307,541

(22) PCT Filed: Jul. 5, 2007

(86) PCT No.: PCT/EP2007/056796
§ 371 (c)(1),
(2), (4) Date: Feb. 12, 2010

(87) PCT Pub. No.: WO2008/003738
PCT Pub. Date: Jan. 10, 2008

(65) Prior Publication Data
US 2010/0130357 A1    May 27, 2010

(30) Foreign Application Priority Data

Jul. 6, 2006  (EP) ..................................... 06356084

(51) Int. Cl.
| | |
|---|---|
| A01N 37/50 | (2006.01) |
| A01N 43/22 | (2006.01) |
| A01N 43/36 | (2006.01) |
| A01N 43/64 | (2006.01) |
| A01N 43/653 | (2006.01) |
| A01N 43/68 | (2006.01) |
| A01N 43/78 | (2006.01) |
| A01N 47/02 | (2006.01) |
| A01N 51/00 | (2006.01) |
| A01N 57/30 | (2006.01) |
| A01P 3/00 | (2006.01) |
| A01P 7/04 | (2006.01) |

(52) U.S. Cl.
USPC ............. 504/100; 514/28; 514/137; 514/245; 514/341; 514/342; 514/357; 514/365; 514/383; 514/407; 514/422; 514/539; 514/242

(58) Field of Classification Search
USPC ............ 504/100; 514/357, 365, 384, 28, 137, 514/242, 245, 341, 342, 383, 407, 422, 539
See application file for complete search history.

(56) References Cited

U.S. PATENT DOCUMENTS 5,034,404 A * 7/1991 Uneme et al. ................. 514/365

FOREIGN PATENT DOCUMENTS

| EP | 1 500 651 | 1/2005 |
|---|---|---|
| WO | 2004/016088 | 2/2004 |
| WO | 2005/077901 | 8/2005 |
| WO | WO 2005/077183 | * 8/2005 |
| WO | WO 2006/128655 | * 12/2006 |

OTHER PUBLICATIONS

Webster's New World Dictionary, 2$^{nd}$ college edition, World Publishing co., New York, 1972, p. 1127.*
International Search Report for PCT/EP2007/056796 dated Aug. 29, 2007, (2 pages).

* cited by examiner

Primary Examiner — John Pak
(74) Attorney, Agent, or Firm — Miles & Stockbridge P.C.

(57) ABSTRACT

A composition comprising at least a pyridylethylbenzamide derivative of general formula (I) (a) and an insecticide compound (b) in a (a)/(b) weight ratio of from 1/1000 to 1000/1. A composition further comprising an additional fungicidal compound.
A method for preventively or curatively combating the pests and diseases of crops by using this composition.

16 Claims, No Drawings

PESTICIDAL COMPOSITION COMPRISING A PYRIDYLETHYLBENZAMIDE DERIVATIVE AND AN INSECTICIDE COMPOUND

CROSS REFERENCE TO RELATED APPLICATIONS

This application is a §371 National Stage Application of PCT/EP2007/056796 filed Jul. 5, 2007 which claims priority from European Application 06356084.1 filed Jul. 6, 2006.

BACKGROUND OF THE INVENTION

1. Field of the Invention

The present invention relates to novel pesticidal compositions comprising a pyridylethylbenzamide derivative and an insecticide compound. The present invention also relates to a method of combating or controlling pests and diseases by applying at a locus infested or liable to be infested such a composition.

2. Description of Related Art

International patent application WO 2004/016088 discloses pyridylethylbenzamide derivatives and their use as fungicide. The possibility of combining one or more of these pyridylethylbenzamide derivatives with known fungicidal or insecticidal products to broaden the spectrum of activity is also disclosed. No specific mention of potential insecticide partner is made in that document neither of any weight ratios in which pyridylethylbenzamide derivative and insecticide partner should be present in that composition.

International patent application WO 2005/077901 discloses fungicide mixtures comprising a pyridylethylbenzamide derivative with a fungicide and a compound capable of inhibiting the transport of electrons of the respiratory chain in phytopathogenic fungal organisms. No mention is made of mixtures comprising a pyridylethylbenzamide derivative with an insecticide active ingredient.

It is always of high-interest in agriculture to use novel pesticidal mixtures showing a broader scope of activity and a fungicide or insecticide synergistic effect in order notably to avoid or to control the development of resistant strains to the active ingredients or to the mixtures of known active ingredients used by the farmer while minimising the doses of chemical products spread in the environment and reducing the cost of the treatment.

SUMMARY OF THE INVENTION

We have now found some novel pesticidal compositions which possess the above mentioned characteristics.

Accordingly, the present invention relates to a composition comprising:
a) a pyridylethylbenzamide derivative of general formula (I)

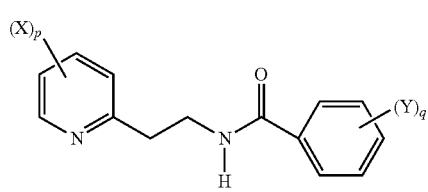

(I)

in which:
p is an integer equal to 1, 2, 3 or 4;
q is an integer equal to 1, 2, 3, 4 or 5;
each substituent X is chosen, independently of the others, as being halogen, alkyl or haloalkyl;
each substituent Y is chosen, independently of the others, as being halogen, alkyl, alkenyl, alkynyl, haloalkyl, alkoxy, amino, phenoxy, alkylthio, dialkylamino, acyl, cyano, ester, hydroxy, aminoalkyl, benzyl, haloalkoxy, halosulphonyl, halothioalkyl, alkoxyalkenyl, alkylsulphonamide, nitro, alkylsulphonyl, phenylsulphonyl or benzylsulphonyl;
as to the N-oxides of the compounds thereof;
and
b) an insecticide compound;
in a (a)/(b) weight ratio of from 1/1000 to 1000/1
with the proviso that insecticide compound is different from compounds of general formula (II)

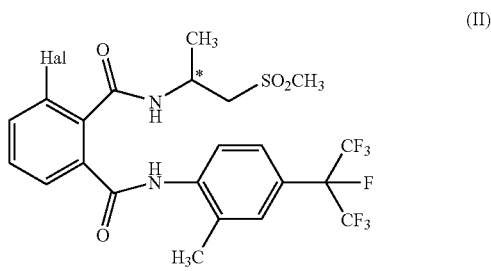

(II)

in which:
Hal represents a chlorine atom, a bromine atom or a iodine atom,
* represents a carbon atom in R- or S-configuration.

DETAILED DESCRIPTION OF A PREFERRED EMBODIMENT

In the context of the present invention:
halogen means chlorine, bromine, iodine or fluorine;
each of the alkyl or acyl radicals present in the molecule contains from 1 to 10 carbon atoms, preferably from 1 to 7 carbon atoms, more preferably from 1 to 5 carbon atoms, and may be linear or branched;
each of the alkenyl or alkynyl radicals present in the molecule contains from 2 to 10 carbon atoms, preferably from 2 to 7 carbon atoms, more preferably from 2 to 5 carbon atoms, and may be linear or branched.

The composition according to the present invention provides a synergistic effect. This synergistic effect allows a reduction of the chemical substances spread into the environment and a reduction of the cost of the pesticidal treatment.

In the context of the present invention, the term "synergistic effect" is defined by Colby according to the article entitled "Calculation of the synergistic and antagonistic responses of herbicide combinations" Weeds, (1967), 15, pages 20-22.

The latter article mentions the formula:

$$E = x + y - \frac{x * y}{100}$$

in which E represents the expected percentage of inhibition of the pest for the combination of the two pesticides at defined doses (for example equal to x and y respectively), x is the percentage of inhibition observed for the pest by the compound (a) at a defined dose (equal to x), y is the percentage of inhibition observed for the pest by the compound (b) at a defined dose (equal to y). When the percentage of inhibition observed for the combination is greater than E, there is a synergistic effect.

The latter article also mentions the formula:

$$E = x + y + z - \frac{(xy + xz + yz)}{100} + \frac{xyz}{10000}$$

in which E represents the expected percentage of inhibition of the pest for the combination of the three pesticides at defined doses (for example equal to x, y and z respectively), x is the percentage of inhibition observed for the pest by the compound (a) at a defined dose (equal to x), y is the percentage of inhibition observed for the pest by the compound (b) at a defined dose (equal to y) and z is the percentage of inhibition observed for the pest by the compound (c) at a defined dose (equal to z). When the percentage of inhibition observed for the combination is greater than E, there is a synergistic effect.

The composition according to the present invention comprises a pyridylethylbenzamide derivative of general formula (I). Preferably, the present invention relates to a composition comprising a pyridylethylbenzamide derivative of general formula (I) in which the different characteristics may be chosen alone or in combination as being:

as regards p, p is 2;
as regards q, q is 1 or 2. More preferably, q is 2;
as regards X, X is chosen, independently of the others, as being halogen or haloalkyl. More preferably, X is chosen, independently of the others, as being a chlorine atom or a trifluoromethyl group;
as regards Y, Y is chosen, independently of the others, as being halogen or haloalkyl. More preferably, Y is chosen, independently of the others, as being a chlorine atom or a trifluoromethyl group;

More preferably, the pyridylethylbenzamide derivative of general formula (I) present in the composition of the present invention is:
—N-{2-[3-chloro-5-(trifluoromethyl)-2-pyridinyl]ethyl}-2-trifluoromethylbenzamide (compound 1);
—N-{2-[3-chloro-5-(trifluoromethyl)-2-pyridinyl]ethyl}-2-iodobenzamide (compound 2); or
—N-{2-[3,5-dichloro-2-pyridinyl]ethyl}-2-trifluoromethylbenzamide (compound 3).

Even more preferably, the pyridylethylbenzamide derivative of general formula (I) present in the composition of the present invention is N-{2-[3-chloro-5-(trifluoromethyl)-2-pyridinyl]ethyl}-2-trifluoromethylbenzamide (compound 1).

The composition according to the present invention comprises an insecticide compound (b). Suitable insecticide are chosen in the following groups:

b1) acetylcholine receptor agonists/antagonists such as chloronicotinyls/neonicotinoids, nicotine, bensultap or cartap. Suitable examples of chloronicotinyls/neonicotinoids include acetamiprid, clothianidin, dinotefuran, imidacloprid, nitenpyram, nithiazine, thiacloprid, thiamethoxam, imidaclothiz and (2E)-1-[(2-chloro-1,3-thiazol-5-yl)methyl]-3,5-dimethyl-N-nitro-1,3,5-triazinan-2-imine;

b2) acetylcholinesterase (AChE) inhibitors such as carbamates and organophosphates. Suitable examples of carbamates include alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, chloethocarb, dimetilan, ethiofencarb, fenobucarb, fenothiocarb, formetanate, furathiocarb, isoprocarb, metam-sodium, methiocarb, methomyl, metolcarb, oxamyl, phosphocarb, pirimicarb, promecarb, propoxur, thiodicarb, thiofanox, triazamate, trimethacarb, XMC and xylylcarb. Suitable examples of organophosphates include acephate, azamethiphos, azinphos (-methyl, -ethyl), bromophos-ethyl, bromfenvinfos (-methyl), butathiofos, cadusafos, carbophenothion, chlorethoxyfos, chlorfenvinphos, chlormephos, chlorpyrifos (-methyl/-ethyl), coumaphos, cyanofenphos, cyanophos, demeton-S-methyl, demeton-S-methylsulphon, dialifos, diazinon, dichlofenthion, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon and vamidothion;

b3) sodium channel modulators/voltage-gated sodium channel blockers such as pyrethroids and oxadiazines. Suitable examples of pyrethroids include acrinathrin, allethrin (d-cis-trans, d-trans), beta-cyfluthrin, bifenthrin, bioallethrin, bioallethrin-S-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha-, beta-, theta-, zeta-), cyphenothrin, DDT, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (1R-isomer), tralocythrin, tralomethrin, transfluthrin, ZXI 8901 and pyrethrins (pyrethrum). Suitable example of oxadiazines includes indoxacarb;

b4) acetylcholine receptor modulators such as spinosyns. Suitable example of spinosyns includes spinosad;

b5) GABA-gated chloride channel antagonists such as cyclodiene organochlorines and fiproles. Suitable examples of cyclodiene organochlorines include camphechlor, chlordane, endosulfan, gamma-HCH, HCH, heptachlor, lindane and methoxychlor. Suitable examples of fiproles include acetoprole, ethiprole, fipronil and vaniliprole;

b6) chloride channel activators such as mectins. Suitable examples of mectins include abamectin, avermectin, emamectin, emamectin-benzoate, ivermectin, lepimectin, milbemectin and milbemycin;

b7) juvenile hormone mimetics such as diofenolan, epofenonane, fenoxycarb, hydroprene, kinoprene, methoprene, pyriproxifen, triprene;

b8) ecdysone agonists/disrupters such as diacylhydrazines. Suitable examples of diacylhydrazines include chromafenozide, halofenozide, methoxyfenozide and tebufenozide;

b9) inhibitors of chitinbiosynthesis such as benzoylureas, buprofezin and cyromazine. Suitable examples of benzoylureas include bistrifluoron, chlorfluazuron, diflubenzuron, fluazuron, flucycloxuron, flufenoxuron, hexaflumuron, lufenuron, novaluron, noviflumuron, penfluoron, teflubenzuron and triflumuron;

b10) inhibitors of oxidative phosphorylation, ATP disrupters such as organotins and diafenthiuron. Suitable examples of organotins include azocyclotin, cyhexatin and fenbutatin oxide;
b11) decouplers of oxidative phosphorylation by disruption of the H proton gradient such as pyrroles and dinitrophenols. Suitable example of pyrroles includes chlorfenapyr. Suitable examples of dinitrophenols include binapacyrl, dinobuton, dinocap and DNOC;
b12) site I electron transport inhibitors such as METIs, hydramethylnone and dicofol. Suitable examples of METIs include fenazaquin, fenpyroximate, pyrimidifen, pyridaben, tebufenpyrad, tolfenpyrad;
b13) site II electron transport inhibitors such as rotenone;
b14) site III electron transport inhibitors such as acequinocyl and fluacrypyrim;
b15) microbial disrupters of the intestinal membrane of insects such as *Bacillus thuringiensis* strains;
b16) inhibitors of lipid synthesis such as tetronic acids and tetramic acids. Suitable examples of tetronic acids include spirodiclofen, spiromesifen and spirotetramat. Suitable example of tetramic acids includes cis-3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester (CAS Reg. No.: 382608-10-8);
b17) carboxamides such as flonicamid;
b18) octopaminergic agonists such as amitraz;
b19) inhibitors of the magnesium-stimulated ATPase such as propargite;
b20) ryanodin receptor agonists such as phthalamides or rynaxapyr. Suitable example of phthalamides includes $N^2$-[1,1-dimethyl-2-(methylsulphonyl)ethyl]-3-iodo-$N^1$-[2-methyl-4-[1,2,2,2-tetrafluoro-1-(trifluoromethyl)ethyl]phenyl]-1,2-benzenedicarboxamide (i.e. flubendiamide, CAS reg. No.: 272451-65-7);
b21) nereistoxin analogues such as thiocyclam hydrogen oxalate and thiosultap-sodium;
b22) biologics, hormones or pheromones such as azadirachtin, *Bacillus* spec., *Beauveria* spec., codlemone, *Metarrhizium* spec., *Paecilomyces* spec., *thuringiensis* and *Verticillium* spec;
b23) active compounds having unknown or non-specified mechanisms of action such as fumigants, selective feeding inhibitors, mite growth inhibitors, amidoflumet; benclothiaz, benzoximate, bifenazate, bromopropylate, buprofezin, chinomethioat, chlordimeform, chlorobenzilate, chloropicrin, clothiazoben, cyclopren, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin, furthermore the compound 3-methylphenyl propylcarbamate (Tsumacide Z), the compound 3-(5-chloro-3-pyridinyl)-8-(2,2,2-trifluoroethyl)-8-azabicyclo[3.2.1]octane-3-carbonitrile (CAS reg. No. 185982-80-3) and the corresponding 3-endo isomer (CAS reg. No. 185984-60-5) (cf. WO 96/37494, WO 98/25923), and also preparations comprising insecticidal effective plant extracts, nematodes, fungi or viruses. Suitable examples of fumigants include aluminium phosphide, methyl bromide and sulphuryl fluoride. Suitable examples of selective feeding inhibitors include cryolite, flonicamid and pymetrozine. Suitable examples of mite growth inhibitors include clofentezine, etoxazole and hexythiazox.

Preferably, the insecticide compound (b) is chosen as being abamectin, acephate, acetamiprid, acrinathrin, aldicarb, alpha-cypermethrin, beta-cyfluthrin, bifenthrin, carbaryl, carbofuran, chlorfenapyr, chlorfluazuron, chlorpyrifos-E, clothianidin, cyfluthrin, cypermethrin, cyromazine, deltamethrin, diflubenzuron, dinotefuran, emamectin benzoate, ethiprole, fenpyroximate, fipronil, flonicamid, flubendiamide, flufenoxuron, gamma-cyhalothrin, hexaflumuron, imidacloprid, indoxacarb, L-cyhalothrin, lepimectin, lufenuron, methamidophos, methiocarb, methomyl, methoxyfenozide, milbemycin, nitenpyram, novaluron, profenofos, pymetrozine, rynaxapyr, spinosad, spirodiclofen, spiromesifen, spirotetramate, tebufenozide, tebufenozide, tebufenpyrad, tebufenpyrad, tebupirimphos, teflubenzuron, tefluthrin, thiacloprid, thiamethoxam, thiodicarb, triazophos triflumuron, imidaclothiz and (2E)-1-[(2-chloro-1,3-thiazol-5-yl)methyl]-3,5-dimethyl-N-nitro-1,3,5-triazinan-2-imine. More preferably, the insecticide compound (b) is chosen as being abamectin, acetamiprid, aldicarb, beta-cyfluthrin, carbofuran, chlorpyrifos-E, clothianidin, cypermethrin, cyromazine, deltamethrin, diflubenzuron, emamectin benzoate, ethiprole, fipronil, gamma-cyhalothrin, imidacloprid, L-cyhalothrin, lufenuron, methiocarb, methoxyfenozide, pymetrozine, rynaxapyr, spinosad, spirodiclofen, spiromesifen, spirotetramate, tebufenozide, tebufenpyrad, tefluthrin, thiacloprid, thiamethoxam, thiodicarb, triflumuron, imidaclothiz and (2E)-1-[(2-chloro-1,3-thiazol-5-yl)methyl]-3,5-dimethyl-N-nitro-1,3,5-triazinan-2-imine. Even more preferably, the insecticide compound (b) is chosen as being abamectin, aldicarb, beta-cyfluthrin, chlorpyrifos-E, clothianidin, cyromazine, deltamethrin, diflubenzuron, emamectin benzoate, fipronil, gamma-cyhalothrin, imidacloprid, L-cyhalothrin, methiocarb, pymetrozine, rynaxapyr, spinosad, spirodiclofen, spiromesifen, spirotetramate, tebufenozide, tebufenpyrad, tefluthrin, thiamethoxam, thiodicarb, imidaclothiz and (2E)-1-[(2-chloro-1,3-thiazol-5-yl)methyl]-3,5-dimethyl-N-nitro-1,3,5-triazinan-2-imine.

Non limitative examples of suitable mixtures according to the present invention may include mixtures of compound 1 with abamectin, compound 1 with acephate, compound 1 with acetamiprid, compound 1 with acrinathrin, compound 1 with aldicarb, compound 1 with alpha-cypermethrin, compound 1 with beta-cyfluthrin, compound 1 with bifenthrin, compound 1 with carbaryl, compound 1 with carbofuran, compound 1 with chlorfenapyr, compound 1 with chlorfluazuron, compound 1 with chlorpyrifos-E, compound 1 with clothianidin, compound 1 with cyfluthrin, compound 1 with cypermethrin, compound 1 with cyromazine, compound 1 with deltamethrin, compound 1 with diflubenzuron, compound 1 with dinotefuran, compound 1 with emamectin benzoate, compound 1 with ethiprole, compound 1 with fenpyroximate, compound 1 with fipronil, compound 1 with flonicamid, compound 1 with flubendiamide, compound 1 with flufenoxuron, compound 1 with gamma-cyhalothrin, compound 1 with hexaflumuron, compound 1 with imidacloprid, compound 1 with indoxacarb, compound 1 with L-cyhalothrin, compound 1 with lepimectin, compound 1 with lufenuron, compound 1 with methamidophos, compound 1 with methiocarb, compound 1 with methomyl, compound 1 with methoxyfenozide, compound 1 with milbemycin, compound 1 with nitenpyram, compound 1 with novaluron, compound 1 with profenofos, compound 1 with pymetrozine, compound 1 with rynaxapyr, compound 1 with spinosad, compound 1 with spirodiclofen, compound 1 with spiromesifen, compound 1 with spirotetramate, compound 1 with tebufenozide, compound 1 with tebufenozide, compound 1 with tebufenpyrad, compound 1 with tebufenpyrad, compound 1 with tebupirimphos, compound 1 with teflubenzuron, compound 1 with tefluthrin, compound 1 with thiacloprid, compound 1 with thiamethoxam, compound 1 with thiodicarb, compound 1 with triazophos, compound 1 with triflumuron, compound 1 with imidaclothiz, compound 1 with (2E)-1-[(2-chloro-1,3-thiazol-5-yl)methyl]3,5-dimethyl-N-nitro-1,3,5-triazinan-2-imine, compound 2 with abamectin, compound 2 with acephate, compound 2 with acetamiprid, compound 2 with acrinathrin, compound 2 with aldicarb, compound 2 with alpha-cypermethrin, compound 2 with beta-cyfluthrin, compound 2 with bifenthrin, compound 2 with carbaryl, compound 2 with carbofuran, compound 2 with chlorfenapyr, compound 2 with chlorfluazuron, compound 2 with chlorpyrifos-E, compound 2 with clothianidin, compound 2 with cyfluthrin, compound 2 with cypermethrin, compound 2 with cyromazine, compound 2 with deltamethrin, compound 2 with diflubenzuron, compound 2 with diflubenzuron, compound 2 with dinotefuran, compound 2 with emamectin benzoate, compound 2 with ethiprole, compound 2 with fenpyroximate, compound 2 with fipronil, compound 2 with flonicamid, compound 2 with flubendiamide, compound 2 with flufenoxuron, compound 2 with gamma-cyhalothrin, compound 2 with hexaflumuron, compound 2 with imidacloprid, compound 2 with indoxacarb, compound 2 with L-cyhalothrin, compound 2 with lepimectin, compound 2 with lufenuron, compound 2 with methamidophos, compound 2 with methiocarb, compound 2 with methomyl, compound 2 with methoxyfenozide, compound 2 with milbemycin, compound 2 with nitenpyram, compound 2 with novaluron, compound 2 with profenofos, compound 2 with pymetrozine, compound 2 with rynaxapyr, compound 2 with spinosad, compound 2 with spirodiclofen, compound 2 with spiromesifen, compound 2 with spirotetramate, compound 2 with tebufenozide, compound 2 with tebufenozide, compound 2 with tebufenpyrad, compound 2 with tebufenpyrad, compound 2 with tebupirimphos, compound 2 with teflubenzuron, compound 2 with tefluthrin, compound 2 with thiacloprid, compound 2 with thiamethoxam, compound 2 with thiodicarb, compound 2 with triazophos, compound 2 with triflumuron, compound 2 with imidaclothiz, compound 2 with (2E)-1-[(2-chloro-1,3-thiazol-5-yl)methyl]-3,5-dimethyl-N-nitro-1,3,5-triazinan-2-imine, compound 3 with abamectin, compound 3 with acephate, compound 3 with acetamiprid, compound 3 with acrinathrin, compound 3 with aldicarb, compound 3 with alpha-cypermethrin, compound 3 with beta-cyfluthrin, compound 3 with bifenthrin, compound 3 with carbaryl, compound 3 with carbofuran, compound 3 with chlorfenapyr, compound 3 with chlorfluazuron, compound 3 with chlorpyrifos-E, compound 3 with clothianidin, compound 3 with cyfluthrin, compound 3 with cypermethrin, compound 3 with cyromazine, compound 3 with deltamethrin, compound 3 with diflubenzuron, compound 3 with diflubenzuron, compound 3 with dinotefuran, compound 3 with emamectin benzoate, compound 3 with ethiprole, compound 3 with fenpyroximate, compound 3 with fipronil, compound 3 with flonicamid, compound 3 with flubendiamide, compound 3 with flufenoxuron, compound 3 with gamma-cyhalothrin, compound 3 with hexaflumuron, compound 3 with imidacloprid, compound 3 with indoxacarb, compound 3 with L-cyhalothrin, compound 3 with lepimectin, compound 3 with lufenuron, compound 3 with methamidophos, compound 3 with methiocarb, compound 3 with methomyl, compound 3 with methoxyfenozide, compound 3 with milbemycin, compound 3 with nitenpyram, compound 3 with novaluron, compound 3 with profenofos, compound 3 with pymetrozine, compound 3 with rynaxapyr, compound 3 with spinosad, compound 3 with spirodiclofen, compound 3 with spiromesifen, compound 3 with spirotetramate, compound 3 with tebufenozide, compound 3 with tebufenozide, compound 3 with tebufenpyrad, compound 3 with tebufenpyrad, compound 3 with tebupirimphos, compound 3 with teflubenzuron, compound 3 with tefluthrin, compound 3 with thiacloprid, compound 3 with thiamethoxam, compound 3 with thiodicarb, compound 3 with triazophos, compound 3 with triflumuron, compound 3 with imidaclothiz and compound 3 with (2E)-1-[(2-chloro-1,3-thiazol-5-yl)methyl]-3,5-dimethyl-N-nitro-1,3,5-triazinan-2-imine.

The composition according to the present invention comprises a compound of general formula (I) (a) and an insecticide compound (b) in a (a)/(b) weight ratio of from 1/1000 to 1000/1. Preferably, (a)/(b) weight ratio is of from 1/125 to 125/1. Even more preferably, (a)/(b) weight ratio is of from 1/25 to 25/1.

The composition of the present invention may further comprise at least one other different fungicide active ingredient (c).

Examples of suitable fungicide mixing partners may be selected in the following list:

c1) a compound capable to inhibit the nucleic acid synthesis like benalaxyl, benalaxyl-M, bupirimate, chiralaxyl, clozylacon, dimethirimol, ethirimol, furalaxyl, hymexazol, mefenoxam, metalaxyl, metalaxyl-M, ofurace, oxadixyl, oxolinic acid;

c2) a compound capable to inhibit the mitosis and cell division like benomyl, carbendazim, diethofencarb, ethaboxam, fuberidazole, pencycuron, thiabendazole thiophanate-methyl, zoxamide;

c3) a compound capable to inhibit the respiration for example
as CI-respiration inhibitor like diflumetorim;
as CII-respiration inhibitor like boscalid, carboxin, fenfuram, flutolanil, furametpyr, furmecyclox, mepronil, oxycarboxine, penthiopyrad, thifluzamide;
as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

c4) a compound capable of to act as an uncoupler like dinocap, fluazinam, meptyldinocap;

c5) a compound capable to inhibit ATP production like fentin acetate, fentin chloride, fentin hydroxide, silthiofam;

c6) a compound capable to inhibit AA and protein biosynthesis like andoprim, blasticidin-S, cyprodinil, kasugamycin, kasugamycin hydrochloride hydrate, mepanipyrim, pyrimethanil;

c7) a compound capable to inhibit the signal transduction like fenpiclonil, fludioxonil, quinoxyfen;

c8) a compound capable to inhibit lipid and membrane synthesis like biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl, vinclozolin;

c9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

c10) a compound capable to inhibit cell wall synthesis like benthiavalicarb, bialaphos, dimethomorph, flumorph, iprovalicarb, mandipropamid, polyoxins, polyoxorim, validamycin A;

c11) a compound capable to inhibit melanine biosynthesis like carpropamid, diclocymet, fenoxanil, phthalide, pyroquilon, tricyclazole;

c12) a compound capable to induce a host defence like acibenzolar-S-methyl, probenazole, tiadinil;

c13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

c14) a compound selected in the following list: (2E)-2-(2-{[6-(3-chloro-2-methylphenoxy)-5-fluoropyrimidin-4-yl]oxy}phenyl)-2-(methoxyimino)-N-methylacetamide, (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, 1-(4-chlorophenyl)-2-(1H-1,2,4-triazol-1-yl)cycloheptanol, 1-[(4-methoxyphenoxy)methyl]-2,2-dimethylpropyl-1H-imidazole-1-carboxylate, 2,3,5,6-tetrachloro-4-(methylsulfonyl)pyridine, 2-butoxy-6-iodo-3-propyl-4H-chromen-4-one, 2-chloro-N-(1,1,3-trimethyl-2,3-dihydro-1H-inden-4-yl)nicotinamide, 2-phenylphenol and salts, 3,4,5-trichloropyridine-2,6-dicarbonitrile, 3,4-dichloro-N-(2-cyanophenyl)isothiazole-5-carboxamide, 3-[5-(4-chlorophenyl)-2,3-dimethylisoxazolidin-3-yl]pyridine, 5-chloro-6-(2,4,6-trifluorophenyl)-N-[(1R)-1,2,2-trimethylpropyl][1,2,4]triazolo[1,5-a]pyrimidin-7-amine, 5-chloro-7-(4-methylpiperidin-1-yl)-6-(2,4,6-trifluorophenyl) [1,2,4]triazolo[1,5-a]pyrimidine, 5-chloro-N-[(1R)-1,2-dimethylpropyl]-6-(2,4,6-trifluorophenyl)[1,2,4]triazolo[1,5-a]pyrimidin-7-amine, 8-hydroxyquinoline sulfate, benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ferimzone, flumetover, fluopicolide, fluoroimide, flusulfamide, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl 1-(2,2-dimethyl-2,3-dihydro-1H-inden-1-yl)-1H-imidazole-5-carboxylate, methyl isothiocyanate, metrafenone, mildiomycin, N-[2-(1,3-dimethylbutyl)phenyl]-5-fluoro-1,3-dimethyl-1H-pyrazole-4-carboxamide, N-(3',4'-dichloro-5-fluorobiphenyl-2-yl)-3-(difluoromethyl)-1-methyl-1H-pyrazole-4-carboxamide, N-(3-ethyl-3,5,5-trimethylcyclohexyl)-3-(formylamino)-2-hydroxybenzamide, N-(4-chloro-2-nitrophenyl)-N-ethyl-4-methylbenzenesulfonamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloronicotinamide, N-[1-(5-bromo-3-chloropyridin-2-yl)ethyl]-2,4-dichloronicotinamide, N-[1-(5-bromo-3-chloropyridin-2-yl) ethyl]-2-fluoro-4-iodonicotinamide, N-[2-(4-{[3-(4-chlorophenyl)prop-2-yn-1-yl]oxy}-3-methoxyphenyl) ethyl]-N<-(methylsulfonyl)valinamide, N-{(Z)-[(cyclopropylmethoxy)imino][6-(difluoromethoxy)-2,3-difluorophenyl]methyl}-2-phenylacetamide, N-{2-[1,1'-bi (cyclopropyl)-2-yl]phenyl}-3-(difluoromethyl)-, 1-methyl-1H-pyrazole-4-carboxamide, N-{2-[3-chloro-5-(trifluoromethyl)pyridin-2-yl]ethyl}-2-(trifluoromethyl) benzamide, natamycin, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, nickel dimethyldithiocarbamate, nitrothal-isopropyl, O-{1-[(4-methoxyphenoxy)methyl]-2,2-dimethylpropyl}1H-imidazole-1-carbothioate, octhilinone, oxamocarb, oxyfenthiin, pentachlorophenol and salts, phosphorous acid and its salts, piperalin, propamocarb fosetylate, propanosine-sodium, proquinazid, pyribencarb, pyrrolnitrine, quintozene, tecloftalam, tecnazene, triazoxide, trichlamide, valiphenal, zarilamid.

Preferably, fungicidal active ingredient (c) is selected from 5-fluoro-1,3-dimethyl-N-[2-(1,3-dimethyl)-but-2-ol-yl]-1H-pyrazole-4-carboxamide, benalaxyl, benalaxyl-M, benthiavalicarb, carboxin, chlorothalonil, cyazofamid, cymoxanil, dimetomorph, fluazinam, fludioxonil, fluquinconazole, fluoxastrobin, flutriafol, fosetyl-aluminium, hexaconazole, hymexazole, ipconazole, mancozeb, mandipropamid, maneb, mefenoxam, metiram, metalaxyl, metalaxyl-M, peconazole, penthiopyrad, phosphorous acid, propamocarb-.HCl, propineb, prothioconazole, tebuconazole, thiram, triadimenol, trifloxystrobin and triticonazole. More preferably, fungicidal active ingredient (c) is selected from 5-fluoro-1,3-dimethyl-N-[2-(1,3-dimethyl)-but-2-ol-yl]-1H-pyrazole-4-carboxamide, fludioxonil, fluquinconazole, fluoxastrobin, ipconazole, prothioconazole, tebuconazole, triadimenol, trifloxystrobin and triticonazole.

Where the third active ingredient (c) as defined above is present in the composition, this compound may be present in an amount of (a):(b):(c) weight ratio of from 1:0.001:0.001 to 1:1000:1000; the ratios of compound (a) and compound (c) varying independently from each other. Preferably, the (a):(b):(c) weight ratio may be of from 1:0.01:0.01 to 1:100:100. More preferably, the (a):(b):(c) weight ratio may be of from 1:0.05:0.05 to 1:80:80.

Following compositions may be cited to illustrate in a non-limited manner the present invention: compound 1 with 5-fluoro-1,3-dimethyl-N-[2-(1,3-dimethyl)-but-2-ol-yl]-1H-pyrazole-4-carboxamide and clothianidin, compound 1 with benalaxyl and clothianidin, compound 1 with benalaxyl-M and clothianidin, compound 1 with benthiavalicarb and clothianidin, compound 1 with carboxin and clothianidin, compound 1 with chlorothalonil and clothianidin, compound 1 with cyazofamid and clothianidin, compound 1 with cymoxanil and clothianidin, compound 1 with dimetomorph and clothianidin, compound 1 with fluazinam and clothianidin, compound 1 with fludioxonil and clothianidin, compound 1 with fluquinconazole and clothianidin, compound 1 with fluoxastrobin and clothianidin, compound 1 with flutriafol and clothianidin, compound 1 with fosetyl-aluminium and clothianidin, compound 1 with hexaconazole and clothianidin, compound 1 with hymexazole and clothianidin, compound 1 with ipconazole and clothianidin, compound 1 with mancozeb and clothianidin, compound 1 with mandipropamid and clothianidin, compound 1 with maneb and clothianidin, compound 1 with mefenoxam and clothianidin, compound 1 with metiram and clothianidin, compound 1 with metalaxyl and clothianidin, compound 1 with metalaxyl-M and clothianidin, compound 1 with peconazole and clothianidin, compound 1 with penthiopyrad and clothianidin, compound 1 with phosphorous acid and clothianidin, compound 1 with propamocarb.HCl and clothianidin, compound 1 with propineb and clothianidin, compound 1 with prothioconazole and clothianidin, compound 1 with tebuconazole and clothianidin, compound 1 with thiram and clothianidin, compound 1 with triadimenol and clothianidin, compound 1 with trifloxystrobin and clothianidin, compound 1 with triticonazole and clothianidin, compound 1 with 5-fluoro-1,3-dimethyl-N-[2-(1,3-dimethyl)-but-2-ol-yl]-1H-pyrazole-4-carboxamide and imidacloprid, compound 1 with benalaxyl and imidacloprid, compound 1 with benalaxyl-M and imidacloprid, compound 1 with benthiavalicarb and imidacloprid, compound 1 with carboxin and imidacloprid, compound 1 with chlorothalonil and imidacloprid, compound 1 with cyazofamid and imidacloprid, compound 1 with cymoxanil and imidacloprid, compound 1 with dimetomorph and imidacloprid, compound 1 with fluazinam and imidacloprid, compound 1 with fludioxonil and imidacloprid, compound 1 with fluquinconazole and imidacloprid, compound 1 with fluoxastrobin and imidacloprid, compound 1 with flutriafol and imidacloprid, compound 1 with fosetyl-aluminium and imidacloprid, compound 1 with hexaconazole and imidacloprid, compound 1 with hymexazole and imidacloprid, compound 1 with ipconazole and imidacloprid, compound 1 with mancozeb and imidacloprid, compound 1 with mandipropamid and imidacloprid, compound 1 with maneb and imidacloprid, compound 1 with mefenoxam and imidacloprid, compound 1 with metiram and imidacloprid, compound 1 with metalaxyl and imidacloprid, compound 1 with metalaxyl-M and imidacloprid, compound 1 with peconazole and imidacloprid, compound 1 with penthiopyrad and imidacloprid, compound 1 with phosphorous acid and imidacloprid, compound 1 with propamocarb.HCl and imidacloprid, compound 1 with propineb and imidacloprid, compound 1 with prothioconazole and imidacloprid, compound 1 with tebuconazole and imidacloprid, compound 1 with thiram and imidacloprid, compound 1 with triadimenol and imidacloprid, compound 1 with trifloxystrobin and imidacloprid, compound 1 with triticonazole and imidacloprid, compound 1 with 5-fluoro-1,3-dimethyl-N-[2-(1,3-dimethyl)-but-2-ol-yl]-1H-pyrazole-4-carboxamide and thiamethoxam, compound 1 with benalaxyl and thiamethoxam, compound 1 with benalaxyl-M and thiamethoxam, compound 1 with benthiavalicarb and thiamethoxam, compound 1 with carboxin and thiamethoxam, compound 1 with chlorothalonil and thiamethoxam, compound 1 with cyazofamid and thiamethoxam, compound 1 with cymoxanil and thiamethoxam, compound 1 with dimetomorph and thiamethoxam, compound 1 with fluazinam and thiamethoxam, compound 1 with fludioxonil and thiamethoxam, compound 1 with fluquinconazole and thiamethoxam, compound 1 with fluoxastrobin and thiamethoxam, compound 1 with flutriafol and thiamethoxam, compound 1 with fosetyl-aluminium and thiamethoxam, compound 1 with hexaconazole and thiamethoxam, compound 1 with hymexazole and thiamethoxam, compound 1 with ipconazole and thiamethoxam, compound 1 with mancozeb and thiamethoxam, compound 1 with mandipropamid and thiamethoxam, compound 1 with maneb and thiamethoxam, compound 1 with mefenoxam and thiamethoxam, compound 1 with metiram and thiamethoxam, compound 1 with metalaxyl and thiamethoxam, compound 1 with metalaxyl-M and thiamethoxam, compound 1 with peconazole and thiamethoxam, compound 1 with penthiopyrad and thiamethoxam, compound 1 with phosphorous acid and thiamethoxam, compound 1 with propamocarb.HCl and thiamethoxam, compound 1 with propineb and thiamethoxam, compound 1 with prothioconazole and thiamethoxam, compound 1 with tebuconazole and thiamethoxam, compound 1 with thiram and thiamethoxam, compound 1 with triadimenol and thiamethoxam, compound 1 with trifloxystrobin and thiamethoxam and compound 1 with triticonazole and thiamethoxam.

The composition according to the present invention may further comprise an other additional component such as an agriculturally acceptable support, carrier or filler.

In the present specification, the term "support" denotes a natural or synthetic, organic or inorganic material with which the active material is combined to make it easier to apply, notably to the parts of the plant. This support is thus generally inert and should be agriculturally acceptable. The support may be a solid or a liquid. Examples of suitable supports include clays, natural or synthetic silicates, silica, resins, waxes, solid fertilisers, water, alcohols, in particular butanol, organic solvents, mineral and plant oils and derivatives thereof. Mixtures of such supports may also be used.

The composition may also comprise other additional components. In particular, the composition may further comprise a surfactant. The surfactant can be an emulsifier, a dispersing agent or a wetting agent of ionic or non-ionic type or a mixture of such surfactants. Mention may be made, for example, of polyacrylic acid salts, lignosulphonic acid salts, phenolsulphonic or naphthalenesulphonic acid salts, polycondensates of ethylene oxide with fatty alcohols or with fatty acids or with fatty amines, substituted phenols (in particular alkylphenols or arylphenols), salts of sulphosuccinic acid esters, taurine derivatives (in particular alkyl taurates), phosphoric esters of polyoxyethylated alcohols or phenols, fatty acid esters of polyols, and derivatives of the above compounds containing sulphate, sulphonate and phosphate functions. The presence of at least one surfactant is generally essential when the active material and/or the inert support are water-insoluble and when the vector agent for the application is water. Preferably, surfactant content may be comprised between 5% and 40% by weight of the composition.

Additional components may also be included, e.g. protective colloids, adhesives, thickeners, thixotropic agents, penetration agents, stabilisers, sequestering agents. More generally, the active materials can be combined with any solid or liquid additive, which complies with the usual formulation techniques.

In general, the composition according to the invention may contain from 0.05 to 99% (by weight) of active material, preferably 10 to 70% by weight.

Compositions according to the present invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra low volume (ulv) liquid, ultra low volume (ulv) suspension, water dispersible granules or tablets, water dispersible powder for slurry treatment, water soluble granules or tablets, water soluble powder for seed treatment and wettable powder.

These compositions include not only compositions which are ready to be applied to the plant or seed to be treated by means of a suitable device, such as a spraying or dusting device, but also concentrated commercial compositions which must be diluted before they are applied to the crop.

The pesticidal compositions of the present invention can be used to curatively or preventively control phytopathogenic fungi of crops but also to curatively or preventively control insects.

Thus, according to a further aspect of the present invention, there is provided a method for preventively or curatively controlling phytopathogenic fungi of crops but also to curatively or preventively control insects characterised in that an effective and non-phytotoxic amount of a composition as hereinbefore defined is applied via seed treatment, foliar application, stem application or drench/drip application (chemigation) to the seed, the plant and/or to the fruit of the plant or to soil and/or to inert substrate (e.g. inorganic substrates (e.g. sand, rockwool, glasswool, expanded minerals (e.g. perlite, vermiculite, zeolite, expanded clay)), Pumice, Pyroclastic materials/tuff, synthetic organic substrates (e.g. Polyurethane), organic substrates (e.g. peat, composts, tree waste products (e.g. coir, wood fibre/chips, tree bark)) and/or to a liquid substrate (e.g. floating hydroponic systems, Nutrient Film Technique, Aeroponics) in which the plant is growing or in which it is desired to grow.

The expression "effective and non-phytotoxic amount" means an amount of composition according to the invention which is sufficient to control or destroy the pests and/or diseases present or liable to appear on the crops, and which does not entail any appreciable symptom of phytotoxicity for the said crops. Such an amount can vary within a wide range depending on the pests and diseases to be combated or controlled, the type of crop, the climatic conditions and the compounds included in the composition according to the invention.

This amount can be determined by systematic field trials, which are within the capabilities of a person skilled in the art.

The method of treatment according to the present invention is useful to treat propagation material such as tubers or rhizomes, but also seeds, seedlings or seedlings pricking out and plants or plants pricking out. This method of treatment can also be useful to treat roots. The method of treatment according to the present invention can also be useful to treat the overground parts of the plant such as trunks, stems or stalks, leaves, flowers and fruits of the concerned plant.

Among the plants that can be protected by the method according to the present invention, mention may be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

Among the diseases of plants or crops that can be controlled by the method according to the present invention, mention may be made of:

Powdery mildew diseases such as:
  *Blumeria* diseases, caused for example by *Blumeria graminis*;
  *Leveillula* diseases, caused for example by *Leveillula taurica*
  *Podosphaera* diseases, caused for example by *Podosphaera leucotricha*;
  *Sphaerotheca* diseases, caused for example by *Sphaerotheca fuliginea* or *Sphaerotheca pannosa*;
  *Uncinula* diseases, caused for example by *Uncinula necator*;
Rust diseases such as:
  *Gymnosporangium* diseases, caused for example by *Gymnosporangium sabinae*;
  *Hemileia* diseases, caused for example by *Hemileia vastatrix*;
  *Phakopsora* diseases, caused for example by *Phakopsora pachyrhizi* or *Phakopsora meibomiae*;
  *Puccinia* diseases, caused for example by *Puccinia recondita*;
  *Uromyces* diseases, caused for example by *Uromyces appendiculatus*;
Oomycete diseases such as:
  *Bremia* diseases, caused for example by *Bremia lactucae*;
  *Peronospora* diseases, caused for example by *Peronospora pisi* or *P. brassicae*;
  *Phytophthora* diseases, caused for example by *Phytophthora infestans*;
  *Plasmopara* diseases, caused for example by *Plasmopara viticola*;
  *Pseudoperonospora* diseases, caused for example by *Pseudoperonospora humuli* or *Pseudoperonospora cubensis*;
  *Pythium* diseases, caused for example by *Pythium ultimum*;
Leafspot, leaf blotch and leaf blight diseases such as:
  *Alternaria* diseases, caused for example by *Alternaria solani*;
  *Cercospora* diseases, caused for example by *Cercospora beticola*;
  *Cladiosporium* diseases, caused for example by *Cladiosporium cucumerinum*;
  *Cochliobolus* diseases, caused for example by *Cochliobolus sativus*;
  *Colletotrichum* diseases, caused for example by *Colletotrichum lindemuthanium*;
  *Cycloconium* diseases, caused for example by *Cycloconium oleaginum*;
  *Diaporthe* diseases, caused for example by *Diaporthe citri*;
  *Diplocarpon* diseases, caused for example by *Diplocarpon rosae*
  *Elsinoe* diseases, caused for example by *Elsinoe fawcettii*;
  *Gloeosporium* diseases, caused for example by *Gloeosporium laeticolor*;
  *Glomerella* diseases, caused for example by *Glomerella cingulata*;
  *Guignardia* diseases, caused for example by *Guignardia bidwelli*;
  *Leptosphaeria* diseases, caused for example by *Leptosphaeria maculans*; *Leptosphaeria nodorum*;
  *Magnaporthe* diseases, caused for example by *Magnaporthe grisea*;

*Mycosphaerella* diseases, caused for example by *Mycosphaerella graminicola; Mycosphaerella arachidicola; Mycosphaerella fijiensis;*

*Phaeosphaeria* diseases, caused for example by *Phaeosphaeria nodorum;*

*Pyrenophora* diseases, caused for example by *Pyrenophora teres;*

*Ramularia* diseases, caused for example by *Ramularia collo-cygni;*

*Rhynchosporium* diseases, caused for example by *Rhynchosporium secalis;*

*Septoria* diseases, caused for example by *Septoria apii* or *Septoria lycopercisi;*

*Typhula* diseases, caused for example by *Typhula incarnata;*

*Venturia* diseases, caused for example by *Venturia inaequalis;*

Root and stem diseases such as:

*Corticium* diseases, caused for example by *Corticium graminearum;*

*Fusarium* diseases, caused for example by *Fusarium oxysporum;*

*Gaeumannomyces* diseases, caused for example by *Gaeumannomyces graminis;*

*Rhizoctonia* diseases, caused for example by *Rhizoctonia solani;*

*Tapesia* diseases, caused for example by *Tapesia acuformis;*

*Thielaviopsis* diseases, caused for example by *Thielaviopsis basicola;*

Ear and panicle diseases such as:

*Alternaria* diseases, caused for example by *Alternaria* spp.;

*Aspergillus* diseases, caused for example by *Aspergillus flavus;*

*Cladosporium* diseases, caused for example by *Cladosporium* spp.;

*Claviceps* diseases, caused for example by *Claviceps purpurea;*

*Fusarium* diseases, caused for example by *Fusarium culmorum;*

*Gibberella* diseases, caused for example by *Gibberella zeae;*

*Monographella* diseases, caused for example by *Monographella nivalis;*

Smut and bunt diseases such as:

*Sphacelotheca* diseases, caused for example by *Sphacelotheca reiliana;*

*Tilletia* diseases, caused for example by *Tilletia caries;*

*Urocystis* diseases, caused for example by *Urocystis occulta;*

*Ustilago* diseases, caused for example by *Ustilago nuda;*

Fruit rot and mould diseases such as:

*Aspergillus* diseases, caused for example by *Aspergillus flavus;*

*Botrytis* diseases, caused for example by *Botrytis cinerea;*

*Penicillium* diseases, caused for example by *Penicillium expansum;*

*Sclerotinia* diseases, caused for example by *Sclerotinia sclerotiorum;*

*Verticillium* diseases, caused for example by *Verticillium alboatrum* or *Verticillium fungicola* (mushrooms);

Seed and soilborne decay, mould, wilt, rot and damping-off diseases:

*Alternaria* diseases caused for example by *Alternaria brassicicola;*

*Aphanomyces* diseases caused for example by *Aphanomyces euteiches;*

*Ascochyta* diseases caused for example by *Ascochyta lentis;*

*Aspergillus* diseases caused for example by *Aspergillus flavus;*

*Cladosporium* diseases caused for example by *Cladosporium herbarum;*

*Cochliobolus* diseases caused for example by *Cochliobolus sativus*

(Conidiaform: *Drechslera, Bipolaris* Syn: *Helminthosporium*);

*Colletotrichum* diseases caused for example by *Colletotrichum coccodes;*

*Fusarium* diseases caused for example by *Fusarium culmorum;*

*Gibberella* diseases caused for example by *Gibberella zeae;*

*Macrophomina* diseases caused for example by *Macrophomina phaseolina;*

*Monographella* diseases caused for example by *Monographella nivalis;*

*Penicillium* diseases caused for example by *Penicillium expansum;*

*Phoma* diseases caused for example by *Phoma lingam;*

*Phomopsis* diseases caused for example by *Phomopsis sojae;*

*Phytophthora* diseases caused for example by *Phytophthora cactorum;*

*Pyrenophora* diseases caused for example by *Pyrenophora graminea;*

*Pyricularia* diseases caused for example by *Pyricularia oryzae;*

*Pythium* diseases caused for example by *Pythium ultimum;*

*Rhizoctonia* diseases caused for example by *Rhizoctonia solani;*

*Rhizopus* diseases caused for example by *Rhizopus oryzae;*

*Sclerotium* diseases caused for example by *Sclerotium rolfsii;*

*Septoria* diseases caused for example by *Septoria nodorum;*

*Typhula* diseases caused for example by *Typhula incarnata;*

*Verticillium* diseases caused for example by *Verticillium dahliae;*

Canker, broom and dieback diseases such as:

*Nectria* diseases, caused for example by *Nectria galligena;*

Blight diseases such as:

*Monilinia* diseases, caused for example by *Monilinia laxa;*

Leaf blister or leaf curl diseases such as:

*Taphrina* diseases, caused for example by *Taphrina deformans;*

Decline diseases of wooden plants such as:

Esca diseases, caused for example by *Phaemoniella clamydospora;*

Diseases of flowers and Seeds such as:

*Botrytis* diseases, caused for example by *Botrytis cinerea;*

Diseases of tubers such as:

*Rhizoctonia* diseases, caused for example by *Rhizoctonia solani;*

*Helminthosporium* diseases, caused for example by *Helminthosporium solani.*

The composition according to the present invention is well tolerated by plants, have favourable homeotherm toxicity and are environmentally friendly; it is suitable for protecting plants and plant organs, for increasing harvest yields, for improving the quality of the harvested material and for controlling animal pests, in particular insects, arachnids and nematodes encountered in agriculture, in forests, in gardens and leisure facilities, in the protection of stored products and materials and in the hygiene sector. It is preferably used as crop protection agents. It is active against normally sensitive and resistant species and against all or some stages of development. Among the animal pests that can also be controlled by the method according to the present invention, mention may be made of:

Pest from the order of the Isopoda, for example *Oniscus asellus, Armadillidium vulgare* and *Porcellio scaber;*

Pest from the order of the Diplopoda, for example *Blaniulus guttulatus;*

Pest from the order of the Chilopoda, for example *Geophilus carpophagus* and *Scutigera* spp.;

Pest from the order of the Symphyla, for example *Scutigerella immaculate;*

Pest from the order of the Thysanura, for example *Lepisma saccharina;*

Pest from the order of the Collembola, for example *Onychiurus armatus;*

Pest from the order of the Orthoptera, for example *Acheta domesticus, Gryllotalpa* spp., *Locusta migratoria migratorioides, Melanoplus* spp. and *Schistocerca gregaria;*

Pest from the order of the Blattaria, for example *Blatta orientalis, Periplaneta americana, Leucophaea maderae* and *Blattella germanica;*

Pest from the order of the Dermaptera, for example *Forficula auricularia;*

Pest from the order of the Isoptera, for example *Reticulitermes* spp.;

Pest from the order of the Phthiraptera, for example *Pediculus humanus corporis, Haematopinus* spp., *Linognathus* spp., *Trichodectes* spp., *Damalinia* spp.;

Pest from the order of the Thysanoptera, for example *Hercinothrips femoralis, Thrips tabaci, Thrips palmi, Frankliniella accidentalis;*

Pest from the order of the Heteroptera, for example *Eurygaster* spp., *Dysdercus intermedius, Piesma quadrata, Cimex lectularius, Rhodnius prolixus* and *Triatoma* spp.;

Pest from the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.;

Pest from the order of the Lepidoptera, for example *Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofinannophila pseudospretella, Cacoecia podana, Capua reticulana, Choristoneura fumiferana, Clysia ambiguella, Homona magnanima, Tortrix viridana, Cnaphalocerus* spp. and *Oulema oryzae;*

Pest from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus;*

Pest from the order of the Hymenoptera, for example *Diprion* spp., *Hoplocampa* spp., *Lasius* spp., *Monomorium pharaonis* and *Vespa* spp.;

Pest from the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella fit, Phorbia* spp., *Pegomyia hyoscyami, Ceratitis capitata, Dacus oleae, Tipula paludosa, Hylemyia* spp. and *Liriomyza* spp.;

Pest from the order of the Siphonaptera, for example *Xenopsylla cheopis* and *Ceratophyllus* spp.;

Pest from the class of the Arachnida, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.;

The plant-parasitic nematodes such as *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The composition according to the present invention may also be used against pests and diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds of the present invention, or a composition according to the invention; this includes for example direct application, spraying, dipping, injection or any other suitable means.

The dose of active material usually applied in the treatment according to the present invention is generally and advantageously between 10 and 800 g/ha, preferably between 50 and 300 g/ha for applications in foliar treatment. If a drench/drip application is possible, the dose can be lower, especially in artificial substrates like rockwool or perlite. The dose of active substance applied is generally and advantageously between 0.1 and 200 g per 100 kg of seed, preferably between 0.5 and 150 g per 100 kg of seed in the case of seed treatment. It is clearly understood that the doses indicated above are given as illustrative examples of the invention. A person skilled in the art will know how to adapt the application doses according to the nature of the crop to be treated.

The composition according to the present invention may also be used in the treatment of genetically modified organisms with the compounds according to the invention or the agrochemical compositions according to the invention. Genetically modified plants are plants into whose genome a heterologous gene encoding a protein of interest has been stably integrated. The expression "heterologous gene encoding a protein of interest" essentially means genes which give the transformed plant new agronomic properties, or genes for improving the agronomic quality of the transformed plant.

The present invention will now be illustrated in a non-limiting manner with the following examples.

EXAMPLE 1

Efficacy Against *Aphis gossypii* of a Composition Containing N-{2-[3-chloro-5-(trifluoromethyl)-2-pyridinyl]ethyl}-2-trifluoromethylbenzamide (Compound 1) and fipronil Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cotton leaves (*Gossypium herbaceum*) which are heavily infested by the cotton aphid (*Aphis gossypii*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 and fipronil alone and in a 2/1 weight ratio mixture.

|  | Dose (ppm) | Mortality in % after $1^d$ | Synergism (Colby) |
| --- | --- | --- | --- |
| Compound 1 | 200 | 10 | — |
| Fipronil | 100 | 40 | — |
| Compound 1 + fipronil (Ratio 2/1) | 200 + 100 | 85 | +39 |

According to the Colby method, a synergistic effect of the mixture tested has been observed.

EXAMPLE 2

Efficacy Against *Myzus persicae* of a Composition Containing N-{2-[3-chloro-5-(trifluoromethyl)-2-pyridinyl]ethyl}-2-trifluoromethylbenzamide (Compound 1) and clothianidin Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 and clothianidin alone and in a 125/1 weight ratio mixture.

|  | Dose (ppm) | Mortality in % after $1^d$ | Synergism (Colby) |
| --- | --- | --- | --- |
| Compound 1 | 20 | 0 | — |
| Clothianidin | 0.16 | 10 | — |
| Compound 1 + clothianidin (Ratio 125/1) | 20 + 0.16 | 35 | +25 |

According to the Colby method, a synergistic effect of the mixture tested has been observed.

EXAMPLE 3

Efficacy Against *Myzus persicae* of a Composition Containing N-{2-[3-chloro-5-(trifluoromethyl)-2-pyridinyl]ethyl}-2-trifluoromethylbenzamide (Compound 1) and imidacloprid Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 and imidacloprid alone and in a 1250/1 weight ratio mixture.

|  | Dose (ppm) | Mortality in % after $1^d$ | Synergism (Colby) |
| --- | --- | --- | --- |
| Compound 1 | 200 | 0 | — |
| Imidaclorpid | 0.16 | 30 | — |
| Compound 1 + imidacloprid (Ratio 1250/1) | 200 + 0.16 | 65 | +35 |

According to the Colby method, a synergistic effect of the mixture tested has been observed.

EXAMPLE 4

Efficacy Against *Myzus persicae* of a Composition Containing N-{2-[3-chloro-5-(trifluoromethyl)-2-pyridinyl]ethyl}-2-trifluoromethylbenzamide (Compound 1) and pymetrozine Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 and imidacloprid alone and in a 250/1 weight ratio mixture.

|  | Dose (ppm) | Mortality in % after 1$^d$ | Synergism (Colby) |
| --- | --- | --- | --- |
| Compound 1 | 200 | 0 | — |
| Pymetrozine | 0.8 | 30 | — |
| Compound 1 + pymetrozine (Ratio 250/1) | 200 + 0.8 | 50 | +20 |

According to the Colby method, a synergistic effect of the mixture tested has been observed.

EXAMPLE 5

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and imidacloprid Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and imidacloprid alone and in a 50/1 weight ratio mixture.

|  | Dose (ppm) | Mortality in % after 4$^d$ | Synergism (Colby) |
| --- | --- | --- | --- |
| Compound 1 | 200 | 5 | — |
| Imidacloprid | 4 | 35 | — |
| Compound 1 + imidacloprid (Ratio 50/1) | 200 + 4 | 85 | +46.75 |

According to the Colby method, a synergistic effect of the mixture tested has been observed.

EXAMPLE 6

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and spinosad Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and spinosad alone and in a 250/1 weight ratio mixture.

|  | Dose (ppm) | Mortality in % after 4$^d$ | Synergism (Colby) |
| --- | --- | --- | --- |
| Compound 1 | 200 | 5 | — |
| Spinosad | 0.8 | 50 | — |
| Compound 1 + spinosad (Ratio 250/1) | 200 + 0.8 | 70 | +17.5 |

According to the Colby method, a synergistic effect of the mixture tested has been observed.

EXAMPLE 7

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and clothianidin Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and clothianidin alone and in a 50/1 weight ratio mixture.

|  | Dose (ppm) | Mortality in % after 6$^d$ | Synergism (Colby) |
| --- | --- | --- | --- |
| Compound 1 | 200 | 0 | — |
| Clothianidin | 4 | 20 | — |
| Compound 1 + clothianidin (Ratio 50/1) | 200 + 4 | 60 | +40 |

According to the Colby method, a synergistic effect of the mixture tested has been observed.

EXAMPLE 8

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and cyromazine Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and cyromazine alone and in a 10/1 weight ratio mixture.

|  | Dose (ppm) | Mortality in % after $6^d$ | Synergism (Colby) |
|---|---|---|---|
| Compound 1 | 200 | 0 | — |
| Cyromazine | 20 | 5 | — |
| Compound 1 + cyromazine (Ratio 10/1) | 200 + 20 | 20 | +15 |

According to the Colby method, a synergistic effect of the mixture tested has been observed.

EXAMPLE 9

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and fenamifos Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and fenamifos alone and in a 10/1 weight ratio mixture.

|  | Dose (ppm) | Mortality in % after $6^d$ | Synergism (Colby) |
|---|---|---|---|
| Compound 1 | 200 | 0 | — |
| Fenamifos | 20 | 75 | — |
| Compound 1 + fenamifos (Ratio 10/1) | 200 + 20 | 90 | +15 |

According to the Colby method, a synergistic effect of the mixture tested has been observed.

EXAMPLE 10

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1) and thiacloprid Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 and thiacloprid alone and in a 50/1 weight ratio mixture.

|  | Dose (ppm) | Mortality in % after $6^d$ | Synergism (Colby) |
|---|---|---|---|
| Compound 1 | 200 | 0 | — |
| Thiacloprid | 4 | 25 | — |
| Compound 1 + thiacloprid (Ratio 50/1) | 200 + 4 | 55 | +30 |

According to the Colby method, a synergistic effect of the mixture tested has been observed.

EXAMPLE 11

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and fludioxonil Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and fludioxonil alone and in a (250:1:250) weight ratio mixture.

|  | Dose (ppm) | Mortality in % after $1^d$ | Synergism (Colby) |
| --- | --- | --- | --- |
| Compound 1 | 200 | 0 | — |
| Clothianidin | 0.8 | 70 | — |
| Fludioxonil | 200 | 0 | — |
| Compound 1 + clothianidin + fludioxonil (Ratio 250:1:250) | 200 + 0.8 + 200 | 98 | +28 |

According to the Colby method, a synergistic effect of the mixture tested has been observed.

EXAMPLE 12

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and ipconazole Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and ipconazole alone and in a (250:1:250) weight ratio mixture.

|  | Dose (ppm) | Mortality in % after $1^d$ | Synergism (Colby) |
| --- | --- | --- | --- |
| Compound 1 | 200 | 0 | — |
| Clothianidin | 0.8 | 70 | — |
| Ipconazole | 200 | 0 | — |
| Compound 1 + clothianidin + ipconazole (Ratio 250:1:250) | 200 + 0.8 + 200 | 96.5 | +26.5 |

According to the Colby method, a synergistic effect of the mixture tested has been observed.

EXAMPLE 13

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and triadimenol Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and triadimenol alone and in a (250:1:250) weight ratio mixture.

|  | Dose (ppm) | Mortality in % after $1^d$ | Synergism (Colby) |
| --- | --- | --- | --- |
| Compound 1 | 200 | 0 | — |
| Clothianidin | 0.8 | 70 | — |
| Triadimenol | 200 | 10 | — |
| Compound 1 + clothianidin + triadimenol (Ratio 250:1:250) | 200 + 0.8 + 200 | 85 | +12 |

According to the Colby method, a synergistic effect of the mixture tested has been observed.

EXAMPLE 14

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and prothioconazole Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and prothioconazole alone and in a (250:1:250) weight ratio mixture.

| | Dose (ppm) | Mortality in % after $6^d$ | Synergism (Colby) |
|---|---|---|---|
| Compound 1 | 200 | 0 | — |
| Clothianidin | 0.8 | 55 | — |
| Prothioconazole | 200 | 0 | — |
| Compound 1 + clothianidin + prothioconazole (Ratio 250:1:250) | 200 + 0.8 + 200 | 70 | +15 |

According to the Colby method, a synergistic effect of the mixture tested has been observed.

EXAMPLE 15

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and tebuconazole Solvent: 7 parts by weight of dimethylformamide
Emulsifier: 2 parts by weight of alkylaryl polyglycolether
To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and tebuconazole alone and in a (1250:1:1250) weight ratio mixture.

| | Dose (ppm) | Mortality in % after $6^d$ | Synergism (Colby) |
|---|---|---|---|
| Compound 1 | 200 | 0 | — |
| Clothianidin | 0.16 | 30 | — |
| Tebuconazole | 200 | 0 | — |
| Compound 1 + clothianidin + tebuconazole (Ratio 1250:1:1250) | 200 + 0.16 + 200 | 100 | +70 |

According to the Colby method, a synergistic effect of the mixture tested has been observed.

EXAMPLE 16

Efficacy Against *Myzus persicae* of a Composition Containing N-{2-[3-chloro-5-(trifluoromethyl)-2-pyridinyl]ethyl}-2-trifluoromethylbenzamide (Compound 1), clothianidin and trifloxystrobin Solvent: 7 parts by weight of dimethylformamide
Emulsifier: 2 parts by weight of alkylaryl polyglycolether
To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) which are heavily infested by the green peach aphid (*Myzus persicae*) are treated by being dipped into the preparation of the active compound of the desired concentration.

After the specified period of time, the mortality in % is determined. 100% means that all the aphids have been killed; 0% means that none of the aphids have been killed.

The following table summarises the results obtained when tested compound 1 clothianidin and trifloxystrobin alone and in a (1250:1:1250) weight ratio mixture.

| | Dose (ppm) | Mortality in % after $6^d$ | Synergism (Colby) |
|---|---|---|---|
| Compound 1 | 200 | 0 | — |
| Clothianidin | 0.16 | 30 | — |
| Trifloxystrobin | 200 | 20 | — |
| Compound 1 + clothianidin + trifloxystrobin (Ratio 1250:1:1250) | 200 + 0.16 + 200 | 60 | +16 |

According to the Colby method, a synergistic effect of the mixture tested has been observed.

EXAMPLE 17

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1), clothianidin and prothioconazole Solvent: 7 parts by weight of dimethylformamide
Emulsifier: 2 parts by weight of alkylaryl polyglycolether
To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 clothianidin and prothioconazole alone and in a (1:40:1) weight ratio mixture.

| | Dose (ppm) | Mortality in % after $4^d$ | Synergism (Colby) |
|---|---|---|---|
| Compound 1 | 1 | 0 | — |
| Clothianidin | 4 | 60 | — |
| Prothioconazole | 1 | 0 | — |
| Compound 1 + clothianidin + prothioconazole (Ratio 1:4:1) | 1 + 4 + 1 | 80 | +20 |

According to the Colby method, a synergistic effect of the mixture tested has been observed.

EXAMPLE 18

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1), clothianidin and 5-fluoro-1,3-dimethyl-N-[2-(1,3-dimethyl)-but-2-ol-yl]-1H-pyrazole-4-carboxamide (Compound A)

Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 clothianidin and compound A alone and in a (50:1:50) weight ratio mixture.

|  | Dose (ppm) | Mortality in % after $4^d$ | Synergism (Colby) |
|---|---|---|---|
| Compound 1 | 200 | 15 | — |
| Clothianidin | 4 | 60 | — |
| Compound A | 200 | 0 | — |
| Compound 1 + clothianidin + compound A (Ratio 50:1:50) | 200 + 4 + 200 | 100 | +34 |

According to the Colby method, a synergistic effect of the mixture tested has been observed.

EXAMPLE 19

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1), clothianidin and prothioconazole Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 clothianidin and prothioconazole alone and in a (50:1:50) weight ratio mixture.

|  | Dose (ppm) | Mortality in % after $4^d$ | Synergism (Colby) |
|---|---|---|---|
| Compound 1 | 200 | 15 | — |
| Clothianidin | 4 | 60 | — |
| Prothioconazole | 200 | 0 | — |
| Compound 1 + clothianidin + prothioconazole (Ratio 50:1:50) | 200 + 4 + 200 | 85 | +19 |

According to the Colby method, a synergistic effect of the mixture tested has been observed.

EXAMPLE 20

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1), clothianidin and triadimenol Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 clothianidin and triadimenol alone and in a (1:4:2) weight ratio mixture.

|  | Dose (ppm) | Mortality in % after $6^d$ | Synergism (Colby) |
|---|---|---|---|
| Compound 1 | 0.2 | 0 | — |
| Clothianidin | 0.8 | 0 | — |
| Triadimenol | 0.4 | 0 | — |
| Compound 1 + clothianidin + triadimenol (Ratio 1:4:2) | 0.2 + 0.8 + 0.4 | 65 | +65 |

According to the Colby method, a synergistic effect of the mixture tested has been observed.

EXAMPLE 21

Efficacy Against *Phaedon cochleariae* Larvae of a Composition Containing N-{2-[3-chloro-5-(trifluoromethyl)-2-pyridinyl]ethyl}-2-trifluoromethylbenzamide (Compound 1), clothianidin and fludioxonil Solvent: 7 parts by weight of dimethylformamide
Emulsifier: 2 parts by weight of alkylaryl polyglycolether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound of the desired concentration and are infested with larvae of the mustard beetle (*Phaedon cochleariae*) as long as the leaves are still moist.

After the specified period of time, the mortality in % is determined. 100% means that all the beetle larvae have been killed; 0% means that none of the beetle larvae have been killed.

The following table summarises the results obtained when tested compound 1 clothianidin and fludioxonil alone and in a (50:1:50) weight ratio mixture.

| | Dose (ppm) | Mortality in % after 6$^d$ | Synergism (Colby) |
|---|---|---|---|
| Compound 1 | 200 | 0 | — |
| Clothianidin | 4 | 40 | — |
| Fludioxonil | 200 | 5 | — |
| Compound 1 + clothianidin + fludioxonil (Ratio 50:1:50) | 200 + 4 + 200 | 55 | +12 |

According to the Colby method, a synergistic effect of the mixture tested has been observed.

EXAMPLE 22

Efficacy Against *Gibberella zeae* of a Composition Containing N-{2-[3-chloro-5-(trifluoromethyl)-2-pyridinyl]ethyl}-2-trifluoromethylbenzamide (Compound 1 and Imidacloprid (Test In Vitro—Microtest)

The microtest was performed in liquid medium with potato-dextrose broth (PDB) using microtitre plates.

The active compound is applied as the technical active substance dissolved in methanol.

A spore suspension of *Gibberella zeae* was used for inoculation. After 4 days of incubation by darkness under shaking (10 Hrz), the optical density in each cavity was evaluated with the aid of a microtitre plate reader.

0% means an efficacy which corresponds to that of the control, while an efficacy of 100% means that no fungal growth is observed.

The following table summarises the results obtained when tested compound 1 and imidacloprid alone and in a (1:1) weight ratio mixture.

| | Dose (ppm) | Efficacy in % | Synergism (Colby) |
|---|---|---|---|
| Compound 1 | 3 | 41 | — |
| Imidacloprid | 3 | 22 | — |
| Compound 1 + imidacloprid (Ratio 1:1) | 3 + 3 | 63 | +9 |

According to the Colby method, a synergistic effect of the mixture tested has been observed.

EXAMPLE 23

Efficacy Against *Phytophthora cryptogea* of a Composition Containing N-{2-[3-chloro-5-(trifluoromethyl)-2-pyridinyl]ethyl}-2-trifluoromethylbenzamide (Compound 1) and spinosad (Test In Vitro—Microtest)

The microtest was performed in liquid medium with potato-dextrose broth (PDB) using microtitre plates.

The active compound is applied as the technical active substance dissolved in methanol.

A mycelium suspension of *Phytophthora cryptogea* was used for inoculation. After 4 days of incubation by darkness under shaking (10 Hrz), the optical density in each cavity was evaluated with the aid of a microtitre plate reader.

0% means an efficacy which corresponds to that of the control, while an efficacy of 100% means that no fungal growth is observed.

The following table summarises the results obtained when tested compound 1 and spinosad alone and in a (1:1) weight ratio mixture.

| | Dose (ppm) | Efficacy in % | Synergism (Colby) |
|---|---|---|---|
| Compound 1 | 0.03 | 13 | — |
| Spinosad | 0.03 | 5 | — |
| Compound 1 + spinosad (Ratio 1:1) | 0.03 + 0.03 | 28 | +11 |

According to the Colby method, a synergistic effect of the mixture tested has been observed.

EXAMPLE 24

Efficacy Against *Pyricularia oryzae* of a Composition Containing N-{2-[3-chloro-5-(trifluoromethyl)-2-pyridinyl]ethyl}-2-trifluoromethylbenzamide (Compound 1), clothianidin and prothioconazole (Test In Vitro—Microtest)

The microtest was performed in liquid medium with potato-dextrose broth (PDB) using microtitre plates.

The active compound is applied as the technical active substance dissolved in aceton.

A spore suspension of *Pyricularia oryzae* was used for inoculation. After 3 days of incubation by darkness under shaking (10 Hrz), the optical density in each cavity was evaluated with the aid of a microtitre plate reader.

0% means an efficacy which corresponds to that percentage of the control, while an efficacy of 100% means that no fungal growth is observed.

The following table summarises the results obtained:

| | Dose (ppm) | Efficacy in % | Synergism (Colby) |
|---|---|---|---|
| Compound 1 + chlothianidin (ratio 1:1) | 0.3 + 0.3 | 25 | — |
| Prothiconazole | 0.015 | 12 | — |
| Compound 1 + chlothianidin + prothioconazole (Ratio 1:1:0.05) | 0.3 + 0.3 + 0.015 | 94 | +60 |

According to the Colby method, a synergistic effect of the mixture tested has been observed.

The invention claimed is:

1. A synergistic composition comprising:
   a) N-{2-[3-chloro-5-(trifluoromethyl)-2-pyridinyl]ethyl}-2-trifluoromethylbenzamide and
   b) an insecticide compound selected from the group consisting of clothianidin, cyromazine, fenamifos, fipronil, imidacloprid, pymetrozine, spinosad, and thiacloprid;
   wherein the (a)/(b) weight ratio is from 1/125 to 125/1;
   with the proviso that said insecticide compound is not a compound of formula (II)

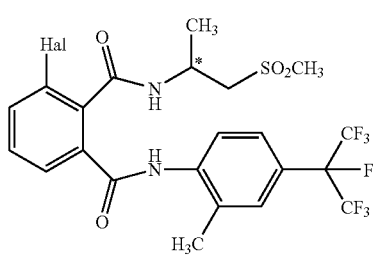

(II)

in which:
Hal represents a chlorine atom, a bromine atom or an iodine atom,
* represents a carbon atom in R- or S-configuration.

2. A composition according to claim 1, further comprising a fungicide compound (c) selected from the group consisting of fludioxonil, ipconazole, triadimenol, prothioconazole, tebuconazole and trifloxystrobin.

3. A composition according to claim 1, further comprising an agriculturally acceptable support, carrier, filler and/or surfactant.

4. A method for controlling insects, said method comprising applying an effective and non-phytotoxic amount of a composition according to claim 1 via seed treatment, foliar application, stem application, drench/drip application and/or by chemigation to the seed, the plant, to the fruit of the plant, to soil, to an inert substrate, Pumice, Pyroclastic materials/tuff, synthetic organic substrates, organic substrates and/or to a liquid substrate in which the plant is growing or in which a plant is desired to grow.

5. Seed treated with a composition of claim 1.

6. A composition according to claim 1, wherein the (a)/(b) weight ratio is from 1/1 to 125/1.

7. A composition according to claim 1, wherein the insecticide is clothianidin.

8. A composition according to claim 1, wherein the insecticide is cyromazine.

9. A composition according to claim 1, wherein the insecticide is fenamifos.

10. A composition according to claim 1, wherein the insecticide is fipronil.

11. A composition according to claim 1, wherein the insecticide is imidacloprid.

12. A composition according to claim 1, wherein the insecticide is pymetrozine.

13. A composition according to claim 1, wherein the insecticide is spinosad.

14. A composition according to claim 1, wherein the insecticide is thiacloprid.

15. The composition according to claim 2, wherein compounds (a), (b) and (c) are present in an amount of (a):(b):(c) weight ratio of from 1:0.01:0.01 to 1:100:100.

16. The composition according to claim 2, wherein compounds (a), (b) and (c) are present in an amount of (a):(b):(c) weight ratio of from 1:0.05:0.05 to 1:80:80.

* * * * *